(12) United States Patent
Mendel-Hartvig et al.

(10) Patent No.: US 7,018,847 B2
(45) Date of Patent: Mar. 28, 2006

(54) ASSAY DEVICE WITH TIMER FUNCTION

(75) Inventors: Ib Mendel-Hartvig, Uppsala (SE); Erik Unger, Uppsala (SE)

(73) Assignee: Pharmacia Diagnostics AB, Uppsala (SE)

( * ) Notice: Subject to any disclaimer, the term of this patent is extended or adjusted under 35 U.S.C. 154(b) by 496 days.

(21) Appl. No.: 09/848,417

(22) Filed: May 4, 2001

(65) Prior Publication Data

US 2002/0001852 A1   Jan. 3, 2002

Related U.S. Application Data

(60) Provisional application No. 60/206,780, filed on May 24, 2000.

(30) Foreign Application Priority Data

May 5, 2000   (SE)   .................................... 0001667

(51) Int. Cl.
*G01N 33/53* (2006.01)
(52) U.S. Cl. ...................... 436/518; 436/514; 436/169; 436/805; 436/810; 435/7.1; 435/7.94; 435/287.1; 435/805; 435/810; 435/970; 422/56; 422/58; 422/61
(58) Field of Classification Search ................ 436/518, 436/514, 169, 805, 810; 435/7.1, 7.94, 287.1, 435/970, 805, 810; 422/56, 58, 61
See application file for complete search history.

(56) References Cited

U.S. PATENT DOCUMENTS 3,954,011 A   5/1976   Manske (Continued)

FOREIGN PATENT DOCUMENTS

EP   0520408 A2   12/1992

(Continued)

OTHER PUBLICATIONS

Webster's Dictionary. pp. 623 and 1210.*

*Primary Examiner*—Bao-Thuy L. Nguyen
(74) *Attorney, Agent, or Firm*—Dinsmore & Shohl LLP

(57) ABSTRACT

An assay device for determining an analyte in an aqueous sample comprises: (i) an elongate flow matrix (6) allowing lateral transport of fluid therethrough by capillary action, wherein the matrix comprises a liquid application zone (3) and downstream thereof, a detection zone (8) having an immobilized capture agent capable of directly or indirectly binding to said analyte, (ii) a wicking member (13) placed at the downstream end of the flow matrix and having an upstream end and a downstream end, and (iii) a time indicator (14) placed downstream of the detection zone (8) for indicating when liquid applied to the liquid application zone has reached the time indicator. The time indicator comprises an indicator substance or substance combination which is capable of exhibiting a visible color change when hydrated by the aqueous sample. The assay device is characterized in that the time indicator (14) is arranged in contact with the wicking member (13) at a variable position between the upstream and downstream ends thereof to thereby permit variation of the time elapsing from the application of the liquid until the indicator substance changes color. A method of performing an assay for determining an analyte in a sample, comprises the steps of flowing sample and assay liquid(s) through the flow matrix of the device such that they reach the detection zone in a predetermined sequence, and when the time indicator has changed color, reading the result of the assay in the detection zone.

11 Claims, 1 Drawing Sheet

U.S. PATENT DOCUMENTS

| | | | |
|---|---|---|---|
| 5,075,078 A | * | 12/1991 | Osikowicz et al. ............ 422/56 |
| 5,229,073 A | * | 7/1993 | Luo et al. ...................... 422/56 |
| 5,415,994 A | * | 5/1995 | Imrich et al. ................... 435/5 |
| 5,602,040 A | * | 2/1997 | May et al. ................... 436/514 |
| 5,785,978 A | * | 7/1998 | Porter et al. ................. 424/401 |
| 6,046,058 A | * | 4/2000 | Sun ............................ 436/514 |
| 6,655,315 B1 | * | 12/2003 | Gattiglia ..................... 116/206 |

FOREIGN PATENT DOCUMENTS

| EP | 0826777 A1 | 3/1998 |
|---|---|---|
| EP | 0915336 A2 | 5/1999 |
| WO | WO8903992 | 5/1989 |

* cited by examiner

ASSAY DEVICE WITH TIMER FUNCTION

This application claims benefit of Provisional Application No. 60/206,780 filed May 24, 2000.

FIELD OF THE INVENTION

The present invention relates to a solid phase assay device comprising a timer function, and to a method of using the device.

BACKGROUND OF THE INVENTION

A type of solid phase assay devices comprises a plate-shaped flow matrix of bibulous material, usually a membrane strip, such as of cellulose nitrate or glass fiber, in which liquid can be transported laterally (i.e. in the plane of the strip) by capillary forces in the membrane. The membrane usually has a sample application zone, and a detection zone downstream of the sample application zone. In the detection zone, usually a capturing reagent for the analyte is immobilized. To conduct an assay, the application zone is contacted with the liquid sample to be assayed for the analyte of interest. The device is maintained under conditions sufficient to allow capillary action of liquid to transport the analyte of interest, if present in the sample, through the membrane strip to the detection zone where the analyte is captured. The capillary liquid flow is usually insured by an absorbing pad or the like at the downstream end of the strip. A detection reagent, usually labelled, is then added upstream of the detection zone and interacts with captured analyte in the detection zone, and the amount of captured analyte is measured. Often, the detection reagent is pre-deposited in or on the membrane strip, e.g. in the form of diffusively movable particles containing fluorophoric or chromogenic groups, either upstream of the sample application zone or between the sample application zone and the detection zone.

Since it takes some time for the sample and the assay liquids to be transported through the detection zone such that the result of the assay can be read, it has been proposed to provide a timing control, such as a "timer" substance or substance combination on the strip which indicates when flow through the flow matrix has occurred or that enough time has elapsed from the time that a fluid sample was applied to the membrane strip for the reading to give a correct value.

EP-A-915 336 discloses a chromatographic assay device wherein the chromatographic medium includes a resolubilizable visible dye in an area between the detection zone and the end of the chromatographic medium, e.g. applied in the absorbing pad. During the performance of the assay, the dye in the dye area is resolubilized and migrates from the dye area to a dye viewing area which gives a visual indication that flow through the chromatographic medium has occurred, such that the assay result can be read and interpreted. The resolubilizable dye may be bound to a first member of a specific binding pair, and a second member of the specific binding pair may be immobilized in the dye viewing area to capture the dye therein. The timing control of EP-A-915 336, however, only indicates that flow through the flow matrix has taken place and does not provide for any adjustment of the time elapsed from the start of the assay until the colour is visible in the viewing area.

This shortcoming is to some extent overcome by the chemical timer disclosed in EP-A-826 777. The chemical timer, which is used in a visible test strip for measuring the concentration of an analyte in a biological fluid that is applied to the strip, measures a predetermined interval chemically and comprises a dry coating of (i) a coloured indicator composition, (ii) a reagent that, when hydrated, is capable of reacting with glucose to change the colour of the indicator, (iii) an inhibitor to inhibit the change in colour of the indicator, and (iv) glucose, in which the inhibitor and glucose concentrations in the dry coating are selected so that the glucose, over a predetermined time after the biological fluid sample is applied to the strip, reacts with the reagent to change the colour of the indicator. When a sample is applied to the strip, hydration of the timer segment composition permits the colour-forming reaction to proceed. The time it takes for the timer segment to change colour is determined by the temperature and by characteristics of the testing reagent, particularly the inhibitor concentration, the amount of glucose, and the hydration and oxygen diffusion rates. The timer also serves as a quality control function, by making it apparent when a test strip has been contaminated by exposure to moisture. Migration of indicators having such a tendency may be prevented by including an ion pairing agent in the matrix.

While the time to colour-change of the chemical timer described in EP-A-826 777 may be varied, this is not readily done, requiring inter alia a different composition of the timer segment for each desired colour-change time. Since the time when the assay result may be reliably read varies between different assay formats depending inter alia on the number of the assay liquids used, there is therefore a need for a test strip having a more flexible timer that can easily be adjusted to a desired indication time to suit the requirements of a particular assay.

SUMMARY OF THE INVENTION

In accordance with the present invention, there is provided an assay device which includes a timer that exhibits a visible colour change when a predetermined time has elapsed from the time that assay liquid, e.g. sample, was applied to the flow matrix, and wherein this predetermined time by simple means may be varied to be adapted to a particular assay format. According to the present invention, this may be accomplished by applying a time indicator on, or in contact with, the absorbing or wicking member at the end of the membrane strip, and in a position along the wicking member that corresponds to a desired value of the time period elapsed from the start of the assay until colour change of the indicator.

In one aspect, the present invention therefore provides an assay device for determining an analyte in an aqueous sample comprising:
(i) a flow matrix having an upstream end and a downstream end and allowing lateral transport of fluid therebetween by capillary action, wherein said matrix comprises a liquid application zone and downstream thereof, a detection zone having an immobilized capture agent capable of directly or indirectly binding to said analyte,
(ii) a wicking member placed at the downstream end of the flow matrix and having an upstream end and a downstream end, and
(iii) a time indicator placed downstream of the detection zone for indicating when liquid applied in the liquid application zone has reached the time indicator, wherein the time indicator comprises an indicator substance or substance combination which is capable of exhibiting a visible colour change when hydrated by the liquid. The device is characterized in that the time indicator is arranged in contact with the wicking member at a variable position between the upstream and downstream ends thereof, thereby permitting variation of the time elapsing from the application of the liquid until the time that the indicator substance or substance combination changes colour.

In a second aspect of the invention, there is provided a method of performing an assay for determining an analyte in a sample, which method comprises the steps of:

(i) providing an assay device as defined above, wherein the time indicator is placed in a selected position between the upstream end and the downstream end of the wicking member adapted to the assay to be performed, (ii) flowing sample and assay liquid(s) through the flow matrix of the device such that they reach the detection zone in a predetermined sequence, and (iii) when the time indicator has changed colour indicating that a predetermined time has elapsed from the application of liquid to the liquid application zone, reading the result of the assay in the detection zone.

The flow matrix is preferably substantially planar, typically rectangular, such as a membrane strip, and allows lateral liquid flow therethrough. Usually, the flow matrix is a chromatographic medium suitable for thin layer chromatography. Exemplary materials are nitrocellulose, nylon, rayon, cellulose, paper or silica. A presently preferred material is nitrocellulose. The flow matrix material can be pretreated or modified as needed.

The wicking member, or absorber, can be made of a bibulous material that will hold a liquid sufficiently so that liquid can be drawn through the flow matrix and accumulate in the wicking member. The size and shape of the wicking member can be chosen according to the volume of liquid used in the assay. Usually, the wicking member is a parallelepipedic pad or the like. Typical materials for the wicking member include, but are not limited to, cellulose and filter paper.

The time indicator may comprise any substance or combination of substances that gives a colour change when hydrated, i.e. when contacted with an aqueous liquid. The term "colour change" includes a change between two distinct colours as well as two different nuances of a single colour. In the present context, also colourless or white is to be understood as representing a colour. The colour change may be caused by the chemical reaction between two, or more, chemical compounds (other than water) or by a pH change. Preferably, however, the indicator substance is a single chemical compound that changes colour when hydrated. In a preferred embodiment, such a chemical indicator is a substance that changes colour depending on the amount of crystal water therein. Thus, the substance may have a first colour when dried, and a second colour when it has taken up crystal water. An exemplary such indicator substance is cobalt dichloride hexahydrate which is bright blue when dehydrated, and pale rose when hydrated.

The indicator substance should be capable of remaining in place when hydrated, at least for a substantial time. If an indicator substance per se has a tendency to migrate, it may be necessary to immobilize or otherwise restrict the mobility of the indicator substance. This may be accomplished by various means well known in the art, e.g. chemical immobilization, bioaffinity-based immobilization etc. The indicator substance may also be allowed to diffuse a small distance before being retarded, e.g. immobilized or captured. An exemplary such indicator substance is patent blue (E131) powder mixed with a filler substance, such as Sephadex®. In dry condition, the mixture is essentially white, whereas the mixture turns blue when the patent blue dye is dissolved and migrates into the Sephadex® gel formed where its migration is retarded. The dry powder mixture may be affixed to the surface of the wicking member by a transparent tape. Alternatively, the patent blue powder may be enclosed by a non-transparent but porous tape, e.g. nonwowen cellulose or a nitrocellulose filter, in which case the patent blue dissolved by the transported fluid will turn the tape blue.

Indicator substances capable of hydration, such as the cobalt dichloride hexahydrate mentioned above, if necessary together with a hygroscopic substance, may also serve as a test that the assay device is viable, since in case of leakage of moisture into the device, which reduces the shelf-life of the device, the indicator substance will change colour. Another example of a time indicator that also will indicate leakage of moisture within the device or from exposure to the exterior is a dry powder mixture consisting of (i) an easily soluble coloured substance, such as the patent blue mentioned above, (ii) a white filler substance in a proportion that gives the powder a white appearance, and (iii) a hygroscopic salt such as calcium chloride dihydrate ($CaCl_2.2H_2O$). The white powder may be affixed to the surface of the wicking member by a transparent and permeable tape. If the tape is of white non-transparent material while still porous and permeable to water vapour, the filler substance may be omitted. Adjustment of the mixture in different ways will make it possible to make the indicator indicate moisture exposure with different stringency. An indicator of this type is non-reversible and will therefore indicate total exposure to moisture in contrast to the above-mentioned cobalt dichloride hexahydrate indicator which is reversible.

The time indicator may be the indicator substance or substance mixture per se, or may be included in or applied to a carrier or other support such as a gel, filter paper strip etc. The application of the time indicator to the assay device may be obtained by various means.

In one embodiment, the indicator substance or substance combination is applied directly to the wicking member, such as by deposition or coating thereon or fixing by tape as mentioned above, for example. In another embodiment, the indicator substance is impregnated or coated to a support, such as a thin filter paper strip, that in turn is applied to the wicking member. Alternatively, if the assay device comprises a housing or cover, the support may be mounted to the inner wall part of the housing that faces the wicking member such that the support contacts the wicking member at a desired position on the surface thereof. The time indicator should, of course, be sufficiently small compared with the extension of the wicking member to permit the time indicator to be placed at a number of different positions in the flow direction of the wicking member.

The time that it takes for an aqueous sample to be transported from the liquid application zone or area of the flow matrix to the time indicator in a given assay device, such that the indicator changes colour, is determined, on the one hand, by the liquid migration rate in the flow matrix and the liquid volume that must pass through the flow matrix, and, on the other hand, by the position of the indicator on the wicking member. By varying the position of the indicator on the wicking member in the flow direction of the assay device, the time elapsing from the liquid application to the indicator change may be shortened or prolonged as desired such that the colour change of the indicator substance takes place only when sufficient time has passed for the analyte measurement or determination in the detection zone to be reliable. A common assay device structure may therefore be provided for use in different assays by placing the indicator strip or reading window at a selected position on the wicking member according to the particular assay to be performed.

The time elapsing until the colour change is also influenced by variation of the thickness, i.e. height, of the wicking member, and this may, if desired, be used to further change the time elapsing until the colour change, e.g. by adding an additional wicking material layer on top of the original wicking member.

DETAILED DESCRIPTION OF THE INVENTION

The assay device according to the present invention is provided with a time indicator that exhibits a colour change when the applied sample or other assay liquid reaches a defined position on a wicking member placed at the end of the flow matrix. In the following, the invention is illustrated applied to an assay device described in our co-pending Swedish patent application No. 9904175-8.

Figure 1:
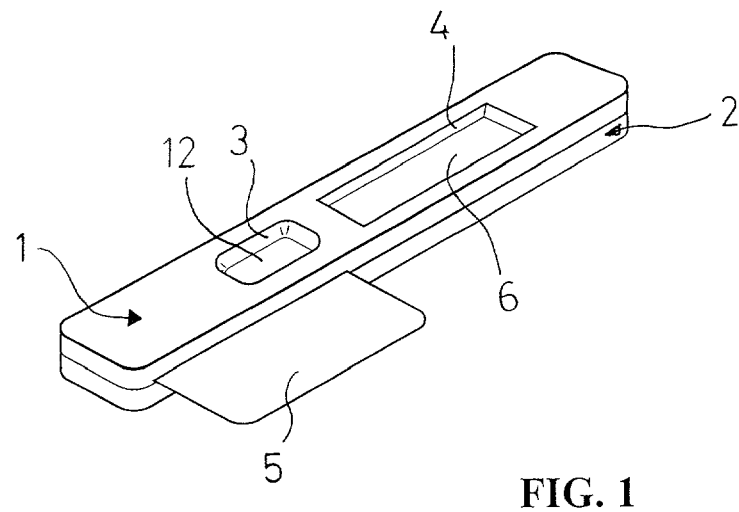
FIG. 1 is a perspective view of an embodiment of a device according to the present invention.
Figure 2:
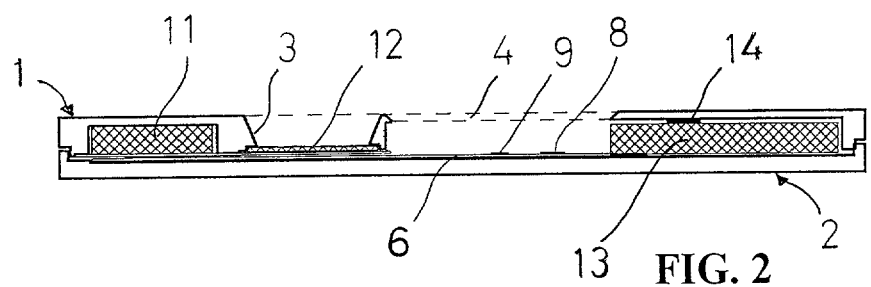
FIG. 2 is a sectional side view of the device in FIG. 1.
Figure 3:
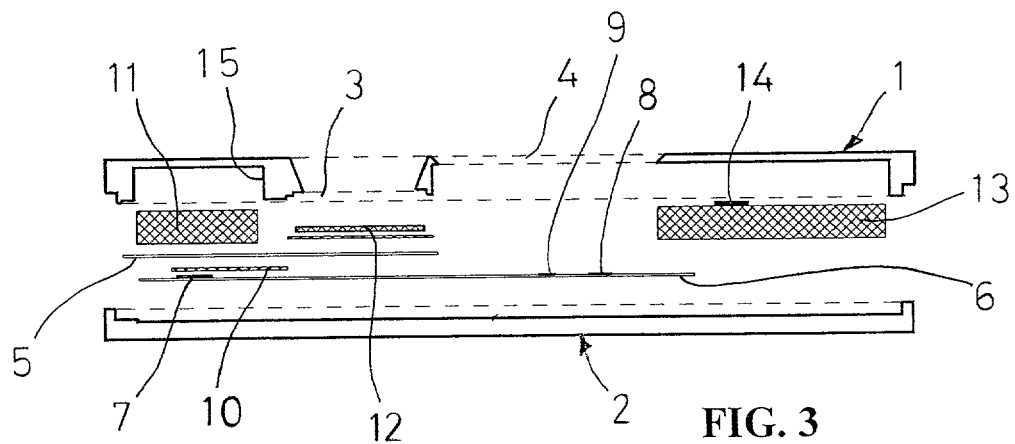
FIG. 3 is an exploded view corresponding to the side view in FIG. 2.

As best shown in FIG. 1, the device illustrated in FIGS. 1 to 3 comprises an upper housing part 1 and lower housing part 2 of a material which is inert with respect to the sample and any reagents used in the assays to be conducted with the device, e.g. polystyrene or polypropylene. The upper housing part 1 has a sample well aperture 3 (here conical) and a detection window 4. Also shown in FIG. 1 is a removable separation means 5 to be described below.

With reference now to FIGS. 2 and 3, the lower housing part 2 has mounted therein a membrane strip 6 of bibulous material (i.e. a porous material susceptible to traversal of an aqueous medium due to capillary action), e.g. nitrocellulose on a polyester backing. Near the upstream end of the strip 6 (to the left in FIGS. 2 and 3), a filter piece 7, containing a diffusively movable detection reagent, is placed on the strip. Such a detection reagent may, for example, be a conjugate between a label particle and a reactant capable of binding to the analyte. Further downstream, and placed below and within the detection window 4, there is a reaction zone 8 on the strip which contains an immobilized reactant capable of binding an analyte to be tested for. In the illustrated case, there is also a calibrator zone 9 containing a predetermined amount of immobilized calibrator substance, for example analyte. Also depicted on the membrane strip 6 is a flow barrier 10, here specifically a piece of a film element, which covers the filter piece 7 and extends towards the opening 3 in the housing part 1. The function of the flow barrier film 10 will be described further on.

The upper housing part 1 contains at the upstream end of the membrane strip 6, a pad 11 of liquid absorbing material intended to serve as a container for flow liquid, or buffer. The opening 3 in housing part 1 (see FIG. 1) is intended for introducing sample to the membrane 6. In the illustrated case, a filter element 12 (which optionally may consist of two or more separate filters), is provided below the opening 3 for assays where the sample liquid needs to be filtered, e.g. when the sample is whole blood and blood cells are to be separated off. The buffer pad 11 thus forms a buffer liquid container, below referred to as buffer pad, and the room defined by the sample opening 3 and the filter element 12 forms a sample well, or sample container.

At the downstream end of the membrane strip 6, a wicking element 13 is placed, here in the form of a pad of absorbent material, such as cellulose, the purpose of which is to assist in maintaining a capillary flow of assay liquids through the membrane strip 6. A thin strip 14 of absorbent material, e.g. filter paper, is mounted in contact with the top of pad 13, e.g. attached to the pad 13 as shown in FIG. 3, or attached to the opposed inner surface area of the housing part 1. The strip 14 contains a substance that changes colour when hydrated, e.g. dehydrated cobalt dichloride hexahydrate. This substance may be applied to the strip by soaking the strip in a solution of the substance and then drying the strip. As will be described below, the strip 14 serves as a chemical time indicator, or chemical timer. At least the portion of the housing part 1 that covers the pad 13 is transparent or translucent or has an opening to permit the colour change of the strip 14 to be observed visually through the cover.

The above-mentioned separation element 5, here a liquid-tight pull-out film, is mounted at the upstream part of the membrane strip 6 to prevent contact between the membrane strip 6 and the bottom parts of the buffer pad 11 and sample filter 12, respectively. The film 5 is arranged to be manually removed by pulling it away from the device to thereby expose the top face of the membrane strip 6 to the buffer pad 11 (except the part of the membrane strip covered by the flow barrier film 10) and the sample filter 12, respectively, such that the membrane strip 6 is brought into simultaneous or close to simultaneous liquid receiving contact with the buffer pad 11 and the filter 12 in the sample well 3. The upper housing part 1 has a recess 15 for the buffer pad 11 designed to press the pad against the pull-out film 5, and thereby against the membrane strip 6 and flow barrier film 10 when the pull-out film 5 is removed. To insure a liquid-tight enclosure of the pad 11 in the recess 15, the pull out film is tightly sealed against the edges of the recess, e.g. by welding. While in the illustrated case above, the pull-out film 5 is intended to be removed completely from the device, it is, of course, sufficient that the film 5 is withdrawn from the membrane strip 6 to such an extent that the membrane strip surface parts in question are exposed to the sample and buffer liquids, respectively.

An assay for an analyte in a sample may be performed with the device described above as follows.

The device is usually provided ready for use with the buffer pad 11 soaked with buffer solution (flow liquid), with the detection reagent pre-deposited in the filter 7, and with the respective appropriate capture reagents immobilized in the reaction (or detection) zone 8 and the calibration zone 9, respectively. If the analyte to be tested for is, say, an antigen, the detection reagent in the filter 7 may, for example, be an antibody to the antigen coupled to a fluorogen-labelled particle, the immobilized reactant in the reaction zone 8 may be an antibody to the antigen, and the calibrator in the calibration zone 9 may be the analyte or an analyte analogue.

A predetermined amount of sample is added through the opening 3 in the housing part 1. All the necessary assay liquids, i.e. in this case sample liquid and buffer liquid, are then present in the device, the pull-out film 5, however, effectively preventing contact between the respective liquids and the membrane strip 6. The assay is then started by the operator removing the pull-out film 5 to thereby put the membrane strip 6 in simultaneous liquid receiving contact with the buffer pad 11 and the sample liquid in the sample well 3.

Buffer liquid from the pad 11 will now penetrate into the membrane strip 6 via the far upstream end part thereof which is in direct contact with the pad 11 (see FIG. 3) and be transported downstream the membrane strip 6 by capillary force. Simultaneously, sample liquid will penetrate into the membrane strip 6 and be transported in the downstream direction of the strip. There will thus be a flow of sample liquid directly followed by a (first) flow pulse of buffer liquid. However, the detection reagent filter 7 and a major part of the buffer pad 11 are separated from the membrane strip 6 by the flow barrier film 10. Buffer liquid that has been transported into the membrane strip 6 will penetrate into and be transported through the filter 7 and bring the detection reagent deposited therein with it, thereby forming a detection reagent flow pulse. This detection reagent flow pulse will follow in sequence after the sample flow and the buffer flow pulse. Buffer that is transported in the membrane strip 6 after the detection reagent has been removed from the filter 7 will form a second buffer flow pulse following after the detection reagent flow pulse.

The above-mentioned different liquid flows will be transported along the membrane strip 6 in the indicated sequence, i.e. sample flow, first buffer flow, detection reagent flow, and second buffer flow, and will eventually reach the calibrator zone 9 and the reaction zone 8. In the reaction zone 8, analyte present in the sample will be captured by the reagent immobilized in the membrane. The analyte/capture reagent complex formed will be washed by the following first buffer flow, and the analyte-reagent complex will then react with detection reagent contained in the detection reagent flow to form a detectable detection reagent/capture reagent complex. The latter will finally be washed by the second buffer flow. In the calibration zone 9, the pre-determined amount of analyte therein will react with the detection reagent in the detection reagent flow to form a detectable detection reagent/analyte complex. The flow liquid from the buffer pad 11 will thus in sequence wash, dissolve and transport detection reagent, and wash.

When the aqueous sample has reached the indicator strip 14 contacting the wicking pad 13, the indicator substance deposited therein changes its colour which can be seen through the transparent or translucent cover or opening therein. The position of the strip 14 has been selected to ensure that all the assay liquids have passed the reaction zone 8 when the liquid front reaches the strip 14 and the colour change takes place. The colour change of the time indicator signals that the assay result may be read. By then measuring, through the detection window formed by the opening 4 in the housing part 1, the signal intensity from the detection reagent captured in the reaction zone 8 and correlating it with that obtained in the calibration zone 9, the amount of analyte in the sample may be determined.

As apparent from the above, an assay with the described device is easy and convenient to perform and provides for simultaneous initiation of the different assay liquid flows. Thus, once the sample has been added to the sample well, the pull-out film may be removed. The liquid in the buffer pad and the sample will thereby be brought into contact with the membrane strip and the desired sequential transport of the different liquid flows will start. The chemical timer then indicates when the assay is completed and it is reliable to read the result of the assay.

In the reaction (or detection) zone described above, a reactant capable of specifically binding the analyte is immobilized (by covalent binding, via physical adsorption, via biospecific affinity, via immobilized particles to which the reactant is covalently bound, etc.). However, instead an agent capable of reacting with the reactant may be immobilized in the membrane, and the reactant may then be added together with the sample, or be pre-deposited in the membrane in an area or zone upstream of the reaction zone. Such an immobilized agent may be one member of a specific binding pair (sbp) and the reactant is then coupled or conjugated to the other member of the spb. Exemplary specific binding pairs include immunological binding pairs, such as antigen-antibody and hapten-antibody, biotin-avidin or -streptavidin, lectin-sugar, hormone-hormone receptor, nucleic acid duplex. For example, the reaction zone may have streptavidin immobilized therein and the capture reactant for the analyte may be biotinylated.

Similarly, the calibration zone may contain a binder for the calibrator substance rather than the calibrator substance per se. The binder is usually a member of a specific binding pair, such as one of those mentioned above, whereas the other member of the specific binding pair is coupled or conjugated to the calibrator substance, which may in turn be added with the sample or pre-deposited upstream of the calibrator zone. Streptavidin, for example, may be immobilized in the calibration zone while the calibrator substance is biotinylated.

For further details on assay devices of the type contemplated herein, and particularly regarding flow matrixes, sequential assays, calibrator systems and detection reagents, it may be referred to our published PCT applications WO 99/36776, WO 99/36777 and WO 99/36780, for example.

Analytes to be determined using the present device are readily apparent to the skilled person. Usually, however, the analyte is a biospecific affinity reactant, e.g. an antibody or other protein, hapten, nucleic acid or polynucleotide, such as a DNA sequence. In the latter case the reaction zone may contain streptavidin and the DNA sequence to which the analyte sequence is to hybridize may be biotinylated.

The present device permits convenient pretreatment of the sample before starting the assay.

The present device may also be adapted for performing assays of the type described in our published PCT application WO 99/60402 where the flow matrix contains a chromatographic separation zone upstream of the reaction (detection) zone to separate sample components which would otherwise disturb or influence the determination of the analyte.

In the following will be described an experiment demonstrating with an assay device described above how the time elapsing from the start of an assay to the colour change varies depending on the position of the chemical timer strip 14 along the wicking pad 13 in the flow direction of the membrane strip 6.

Experiment

Time of Colour Change vs Position of Time Indicator Along the Wicking Pad

A device as shown in FIGS. 1 to 3 was used. The membrane strip 6 was a 5×45 mm nitrocellulose membrane (Whatman, porosity 8 μm) on a polyester backing, the sample filter 12 was a Primecare blood cell/plasma separation membrane, and the buffer pad 11 was a PVA containing 150 μl of buffer (0.1 M Na-phosphate, pH 7.5, 3% BSA, 10% sucrose, 0.15 M NaCl, 0.05% bovine gammaglobulin, 0.05% $NaN_3$). The wicking pad 13 was a double Whatman WF1.5 filter.

To the inner surface of the upper housing part 1, opposite the wicking pad 13 and visible through the transparent housing, were attached by two-sided adhesive tape four filter paper strips 14, each of 1 mm length and 8 mm width, with an interspace of 1 mm at 0, 2, 4 and 6 mm, respectively, from the adjacent edge of the detection window 4. The four filter strips 14 contacted the underlying wicking pad 13, 0 mm being at the upstream edge of the wicking pad 13. The filter paper had previously been soaked with a saturated solution of cobalt dichloride hexahydrate [$COCl_2(H_2O)_6$], and dried for about 15 minutes at 120° C. 80 µl of whole blood were added to the device, and after 20 seconds the pull-out film 5 was pulled off to bring the sample filter 12 and the buffer pad 11 in contact with nitrocellulose strip 6. The time was counted from the removal of the pull-out film until (i) the colour change started, and (ii) half the indicator strip had changed colour. The change of the indicator was from bright blue to pale rose, and after a longer time the colour was washed away. The results are shown in Table 1 below as the average of 4 tests for each strip.

TABLE 1

| Distance from fore edge of wicking filter (mm) | Time to start colour of change (min.) | Time to colour change of half indicator strip (min.) |
| --- | --- | --- |
| 0 | 11.7 | 13.7 |
| 2 | 15.0 | 18.0 |
| 4 | 19.4 | 22.5 |
| 6 | 24.6 | 27.8 |

As appears from the table, the time of the colour change of the indicator strip was proportional to the distance of the indicator strip from the upstream edge of the wicking pad, and varied from about 12 minutes to 25 minutes depending on the position of the indicator strip. This demonstrates that a desired time of colour change can be set by attaching the indicator strip at an appropriate position on the upper housing of the device, or on the wicking pad.

While the invention has been described and pointed out with reference to operative embodiments thereof, it will be understood by those skilled in the art that various changes, modifications, substitutions and omissions can be made without departing from the spirit of the invention. It is intended therefore that the invention embraces those equivalents within the scope of the claims which follow.

The invention claimed is:

1. An assay device for determining an analyte in an aqueous sample comprising:
   (i) an elongate flow matrix allowing lateral transport of fluid therethrough by capillary action, wherein said matrix comprises a liquid application zone and downstream thereof, a detection zone having an immobilized capture agent capable of directly or indirectly binding to said analyte,
   (ii) a wicking member at the downstream end of the flow matrix and having an upstream end and a downstream end,
   (iii) an indicator downstream of the detection zone for indicating when liquid applied in the liquid application zone has reached the indicator, wherein the indicator comprises an indicator substance or substance combination which is capable of exhibiting a visible colour change when hydrated by the aqueous sample, and wherein the indicator is arranged in contact with the wicking member at a variable position between the upstream and downstream ends of the wicking member, thereby permitting variation of the time elapsing from the application of liquid to the liquid application zone until the indicator substance or substance combination changes colour, and
   (iv) a housing enclosing the flow matrix and the wicking member, wherein the indicator is included on an inner side of the housing at a transparent or translucent portion of the housing.

2. The device according to claim 1, wherein the indicator substance comprises a single chemical compound capable of changing colour when absorbing water.

3. The device according to claim 1 or 2, wherein the indicator is included on the wicking member.

4. The device according to claim 1, wherein the indicator includes a hygroscopic substance.

5. The device according to claim 1, wherein the indicator includes a filler substance.

6. The device according to claim 1, wherein the indicator comprises a substance mixture attached to the wicking member or the inner side of the housing by tape.

7. The device according to claim 1, wherein the indicator comprises an indicator substance or substance combination on a support which in turn is included on the wicking member or on an inner side of the housing.

8. The device according to claim 8, wherein the support comprises a strip of solid material.

9. A method of performing an assay for determining an analyte in a sample, the method comprising the steps of:
   (i) providing an assay device as defined in claim 1, wherein the indicator is placed in a selected position between the upstream end and the downstream end of the wicking member adapted to the assay to be performed,
   (ii) flowing sample and assay liquid(s) through the flow matrix of the device such that they reach the detection zone in a predetermined sequence, and
   (iii) when the indicator has changed colour, reading the result of the assay in the detection zone.

10. The device according to claim 9, wherein the support comprises a strip of filter paper.

11. The device according to claim 1, wherein the indicator is positioned in contact with the wicking member in the device at a position such that all assay liquid will have passed the detection zone before assay liquid reaches the indicator.

* * * * *

UNITED STATES PATENT AND TRADEMARK OFFICE
CERTIFICATE OF CORRECTION

| | | |
|---|---|---|
| PATENT NO. | : 7,018,847 B2 | Page 1 of 1 |
| APPLICATION NO. | : 09/848417 | |
| DATED | : March 28, 2006 | |
| INVENTOR(S) | : Ib Mednel-Hartvig et al. | |

It is certified that error appears in the above-identified patent and that said Letters Patent is hereby corrected as shown below:

Claim 1, column 9, line 48, after "matrix", insert --, having an upstream end and a downstream end,--.

Claim 1, column 9, line 53, after "analyte,", insert --the flow matrix further comprising a diffusively movable detection reagent,--.

Claim 1, column 9, line 54, change "wicking member" to --separate wicking member located--.

Claim 1, column 10, line 7, after "in contact with", insert --a top surface of--.

Claim 1, column 10, line 8, after "wicking member", delete "at a variable position between the upstream and downstream ends of the wicking member, thereby permitting variation of the time elapsing from the application of liquid to the liquid application zone until the indicator substance or substance combination changes colour".

Claim 1, column 10, lines 15-16, change "included on an inner side of" to --located within--.

Claim 6, column 10, line 29, delete "or the inner side of the housing".

Claim 7, column 10, line 33, delete "or on the inner side of the housing".

Column 10, line 55, insert --13. The device according to claim 1, wherein the indicator is included on an inner side of the housing.--.

Signed and Sealed this

Eighteenth Day of March, 2008

JON W. DUDAS
*Director of the United States Patent and Trademark Office*